United States Patent [19]

Zigler

[11] Patent Number: 5,379,103

[45] Date of Patent: Jan. 3, 1995

[54] METHOD AND APPARATUS FOR IN SITU DETECTION OF MINUTE AMOUNTS OF TRACE ELEMENTS

[75] Inventor: Arie Zigler, Rishon Lezion, Israel

[73] Assignee: APTI, Inc., Del.

[21] Appl. No.: 57,475

[22] Filed: May 6, 1993

[51] Int. Cl.⁶ .............................. G01N 21/00
[52] U.S. Cl. ..................... 356/73; 356/318; 250/461.1
[58] Field of Search .............. 356/318, 73, 72; 250/461.1

[56] References Cited

U.S. PATENT DOCUMENTS

| | | | |
|---|---|---|---|
| 4,008,388 | 2/1977 | McLafferty et al. | 250/281 |
| 4,753,530 | 6/1988 | Knight et al. | 356/318 |
| 4,802,762 | 2/1989 | Hill, Jr. | 356/318 |
| 4,925,307 | 5/1990 | Cremers et al. | 356/318 |
| 5,042,947 | 8/1991 | Potzschke et al. | 356/318 |

FOREIGN PATENT DOCUMENTS 2154315 9/1985 United Kingdom ............... 356/318

OTHER PUBLICATIONS

Measures, "Laser Remote Chemical Analysis," Fundamentals of Laser Remote Sensing, pp. 1-5.

"Method 1620," United States EPA Office of Water Regulations and Standards, Industrial Technology Division, pp. 1-38 (1989).

Primary Examiner—F. L. Evans
Assistant Examiner—Russell C. Wolfe
Attorney, Agent, or Firm—Parkhurst, Wendel & Rossi

[57] ABSTRACT

A mobile laboratory for in situ detection of organic and heavy metal pollutants in ground water is disclosed. Pulsed laser energy is delivered via fiber optic media to create a laser spark on a remotely located analysis sample, which is irradiated. In a first operational mode, laser energy emitted from an optical delivery system, e.g., a fiber optic media, is focused, for example by one or more lenses, on the surface of an analysis sample, thus generating a plasma. At high temperatures generated by the laser spark, dissociation occurs, allowing the emitted spectrum to be analyzed for the presence of trace elements, such as heavy metals. Because temperature changes after the end of the laser pulse result in a changing spectral characteristic of the sample, signals emitted from the recombining plasma can be used to identify the contents of the sample. In a second mode, the focusing of the laser energy is removed, so that organic molecules with an aromatic structure emit absorbed ultraviolet energy as fluorescence, which is transmitted via fiber optic media for further analysis. The measured wavelength and time characteristics of the emitted fluorescence can be compared against predetermined characteristics to identify the organic substances in the analysis sample.

28 Claims, 5 Drawing Sheets

METHOD AND APPARATUS FOR IN SITU DETECTION OF MINUTE AMOUNTS OF TRACE ELEMENTS

BACKGROUND OF THE INVENTION

1. Field of the Invention

The invention relates to detection of minute amounts of trace elements in a field environment, using laser induced spectroscopy. In particular, the invention relates to a mobile apparatus which allows in situ measurement and data collection of ground water trace element pollutants.

2. Related Art

Raymond Measures in *Laser Remote Chemical Analysis* discloses laser remote sensing including scattering, absorption and fluorescence techniques. Flame spectroscopy has been used to identify metal substances in an analysis sample. A sample is heated to temperatures in the order of several thousands of degrees, causing the metals to emit characteristic resonance lines, which can be used with spectroscopy techniques to detect the presence of very low concentrations of such metals.

In September 1989, the United States Environmental Protection Agency, Office of Water Regulations and Standards, Industrial Technology Division (Office of Water) issued draft Method 1620: Metals by Inductively Coupled Plasma Atomic Emission Spectroscopy and Atomic Absorption Spectroscopy, hereinafter EPA Method 1620. Inductively coupled plasma atomic emission spectroscopy (ICP) is among the methods which have been employed to detect trace elements, such as metals, in solutions, such as ground water and soil samples. ICP has been used for both for simultaneous and sequential determination of trace elements in solution. In the ICP method, samples are nebulized by an ultrasonic instrument, creating an aerosol. The aerosol is transported to a plasma torch, where excitation occurs. Characteristic atomic line spectra are produced by a radio frequency (RF) coupled plasma. The spectra are dispersed by a grating spectrometer and the intensities monitored by photomultiplier tubes. The tube photocurrents are processed and controlled by a computer system.

In addition to the need for transporting the sample, it must also be filtered, acidified and filtered for analysis. Dissolved elements, those which will pass through a 0.45 m membrane filter, are determined in samples that have been filtered and acidified. Background correction techniques may be needed and appropriate steps must be taken in all analyses to assure that interferences are taken into account.

EPA Method 1620 also documents Cold Vapor Atomic Absorption (CVAA) techniques employed for the analysis of mercury. This flameless procedure is based on the absorption of radiation at 253.7 nm by mercury vapor. Using this method, mercury compounds are oxidized and the mercury is reduced to the elemental state and aerated from solution in a closed system. The mercury vapor passes through a cell positioned in the light path of an atomic absorption spectrophotometer. Absorbance (peak height) is measured as a function of mercury concentration. Organic mercurials which may be present will not respond to the CVAA technique, unless they are first broken down and converted to mercuric ions. This requires an oxidation step, using potassium persulfate as the oxidant. In addition, a heating step is required for methyl mercuric chloride when present in or spiked into a natural system. Thus, this method also requires a complicated sample preparation.

EPA Method 1620 also documents GFAA Spectroscopy for analysis of water and soil/sediment samples, as a method for multi-element determination of trace elements in solution. Using this technique, a few microliters of the sample are evaporated at low temperature to remove the solvent from the sample and then ashed at higher temperature (2000°–3000° C.), for example, by a heated conductor. Atomization occurs in a few milliseconds to a few seconds. The absorption or fluorescence of the atomized particles can then be measured in the region above the heated conductor. At the wavelength at which absorption (or fluorescence) occurs, the detector output rises to a maximum after a few seconds of ignition. This is followed by a rapid decay back to zero as the atomization products escape into the surroundings. A high speed recorder is used to monitor the change.

Many organic contaminants in a ground water analysis sample have an aromatic (ring) molecular structure, which efficiently absorbs light and later emits absorbed ultraviolet energy as fluorescence. The intensity, wavelength and time characteristics of the fluorescence waveforms can be used to identify types and concentrations of organics in an analysis sample.

These conventional techniques for the analysis of contaminants in a ground water or other analysis sample involve the application of routine repetitive analysis, such as gas chromatography and mass spectroscopy on samples taken from wells. Such monitoring requires the use of sampling procedures, which must avoid introducing further contaminants into the sample. These conventional techniques are labor intensive because of the long time required for sample preparation, analysis and storage. These approaches are also constrained by the need to remove a sample from its environment and heat the sample to a high temperature. As a result, a labor intensive sampling and analysis process is also required to detect the presence of metals in analysis samples.

Laser produced plasmas, plasmas produced by high power lasers, have been used in various scientific and industrial applications, in particular, material manufacturing, coating materials, painting and in drilling. However, laser produced plasma spectroscopy has not heretofore been used in the detection of pollutants or contaminants in analysis samples.

SUMMARY OF THE INVENTION

The invention seeks to provide a mobile laboratory capable of real time detection of water inorganic and organic pollutants in the field environment. The system can be transported to a location where it can be used as a laboratory, in which case samples are brought to the mobile lab for on site analysis. The system can also be used for in situ measurement, in which case fiber optic media transmit energy to create the necessary conditions in a well or other remote location and to transmit the resulting spectral phenomena to an analyzer in the mobile lab. Typically, laser energy from a laser energy emitter is coupled to an optical delivery system. Examples of such optical delivery systems include systems using mirrors or systems using fiber optic transmission media. For example, in a system using fiber optic transmission media, the excitation fiber transmits light energy to an analysis sample at a remote location. The fiber can be integrated into a penetrator which allows delivery of laser light into ground water, which has been collected into a cell coupled to the fiber optics. In either case organic and inorganic contaminants can be detected.

The invention utilizes a laser based detection system which can be switched to operate in either of two modes. In a first mode, the light from the optical delivery system, e.g., fiber optic media, is focused by, for example, one or more lenses, onto the surface of water or soil at the remote location, for example in a well, or on the sample in the mobile lab. As a result of the high temperature plasma generated, part of the water vaporizes and partial ionization occurs, with the remaining neutral atoms left in excited electron states. In order to improve signal to noise ratio, S/N, the plasma is allowed to cool down by the rapid expansion that retards recombination. Thus, the degree of ionization (excitation) tends to a constant value. However, the plasma temperature that is responsible for the background is reduced. Light radiated from the plasma is transmitted by the optical delivery system, e.g. a second fiber optic media, to a spectral analyzer which can be used with a processor or other device performing time dependent recombination of signals to identify metals or other trace elements in the water or soil analysis sample.

In the second mode, laser light from the excitation portion of the optical delivery system, e.g. the excitation fiber, excites aromatic molecules dissolved in the water causing some of them to fluoresce. To reduce the noise due to the backscatter and thus increase signal to noise ratio, the fluorescence is collected by second portion of the optical delivery system, e.g., a fiber optic media, and is transmitted to high resolution, computerized spectrometer equipment at a base detection center. By comparing the collected emission peaks with stored data, it is possible to identify the organic substances in the analysis sample.

BRIEF DESCRIPTION OF THE DRAWINGS

The above summarized invention will be described in detail with reference to the attached figures in which.

DETAILED DESCRIPTION OF THE PREFERRED EMBODIMENTS

An apparatus for measuring the contents of an analysis sample includes a pulsed laser energy emitter and a means, such as fiber optics and one or more lenses, for delivering and focusing energy emitted from the laser energy emitter onto the analysis sample. Although the embodiment herein discloses using fiber optic transmission media, it will be known to those of ordinary skill that any arrangement of lenses and mirrors or other components can be used which forms an optical energy delivery system suitable for transmitting energy at the levels required.

The rapid heat generated (for example, 5,000° K. for 1 $\mu$sec irradiation at peak intensity of $10^7$ w/cm$^2$) at the focused location generally results in the vaporization of the water and other substances, such as pollutants, contained therein. A plasma is formed at a small portion of the analysis sample. The vapor may be partly ionized and remaining neutral atoms are in left excited electron states. The plasma would reach much higher levels of ionization at higher laser intensity. For example, at higher temperatures (10,000° K. −20,000° K.) this irradiation results in complete dissociation of molecules into atoms. Measurement of the energy spectrum emitted by the plasma identifies the elements contained in the analysis sample.

Thus, the invention is used with a means, such as a spectrum analyzer, for measuring spectral characteristics of light emitted from a sample. The measured spectral characteristics identify the substances in the analysis sample. Measured spectral characteristics can be compared against spectral characteristics stored in a memory to identify the substances in the analysis sample.

In order to provide a remote capability, light from the laser energy emitter is transmitted via fiber optic transmission media to an analysis sample. For example, 1 cm diameter silica glass fiber can withstand intensity up to $10^8$ w/cm$^2$. Fiber optic media is also used to transmit light radiated from the analysis sample to a spectral analyzer. Preferably, separate fiber optic media are used in each direction to prevent backscattering and to increase signal to noise ratio. As discussed further herein, in a first operating mode, laser induced heating of the sample allows spectroscopy techniques to be used to detect metals or other trace elements in the analysis sample. Organic substances are detected in a second operating mode by fluorescence of aromatic molecules. In order to generate a plasma spark, light exiting from the fiber optics will be focused by means of one or more lenses.

Figure 1:
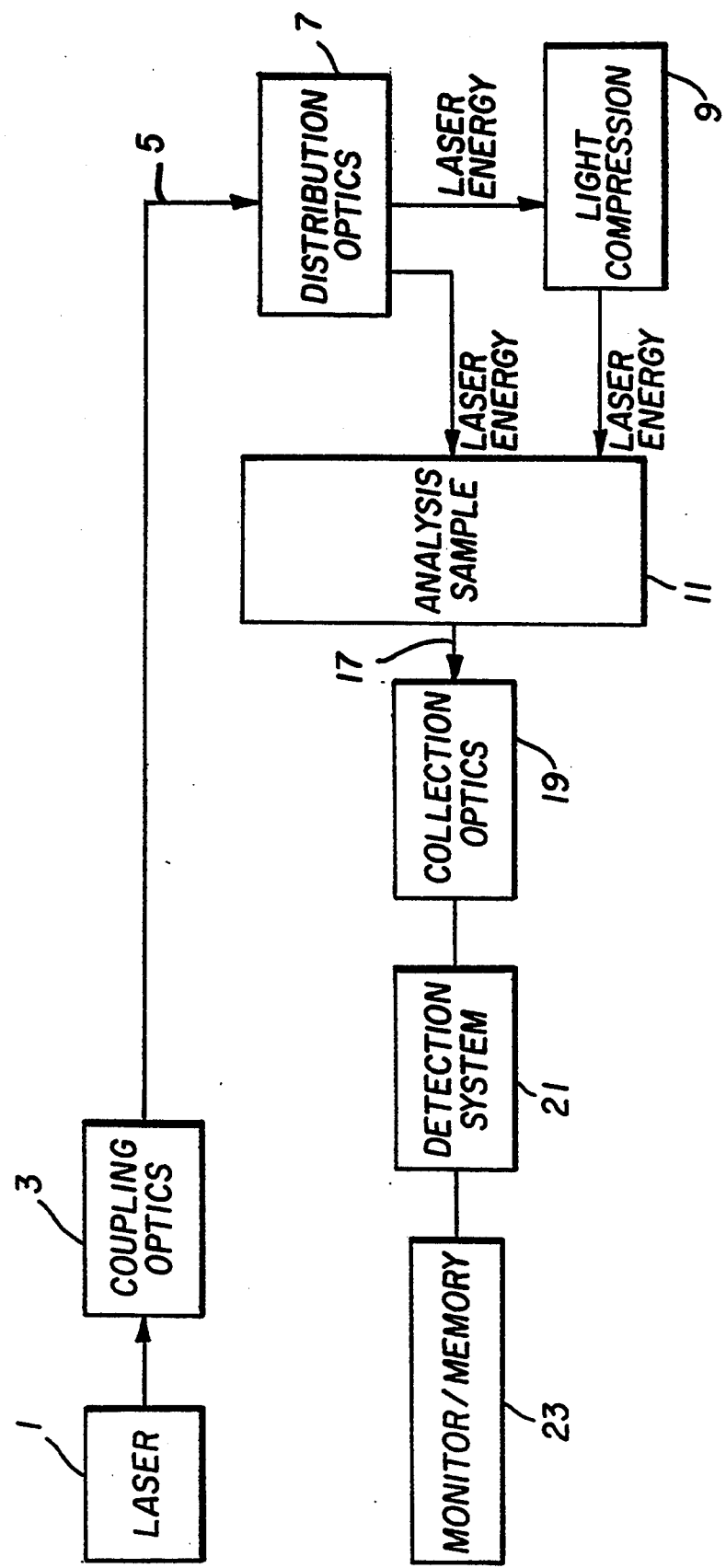
FIG. 1 is an overall block diagram of the invention.

In the block diagram of FIG. 1, the laser energy emitter is from a pulsed laser, which emits bursts of laser energy to create a laser spark. One such laser energy emitter is an excimer (XeCl) laser emitting a wavelength of 308 nm and pulsed by a pulsing device to generate pulses between 0.01 microsecond and 0.1 microsecond in duration at a rate of 100 times per second. The laser is capable of delivering 0.5 joule in 0.01–0.1 $\mu$sec. The laser need not be a high energy laser, but must generate high peak power that can be focused to about $10^9$ W/cm$^2$. The excimer laser offers a mature technology for remote sensing applications where high average power and peak power ultraviolet radiation is required. Thus, it is also a useful choice for triggering fluorescence of aromatic molecules. Another possible laser choice is the Nd:YAG laser capable of delivering 0.3 joule in 10 nanoseconds at a rate of 10 pulses per second. The laser frequency can be doubled or tripled by means of non-linear crystals. The selection of the particular laser to be used in a given application will determine the pulse width and pulse repetition rate required to achieve the desired levels of intensity.

Laser energy is coupled from emitter 1 through coupling optics 3 to fiber optic transmission media 5. Fiber optic transmission media 5 transmits the laser energy to distribution optics 7. Distribution optics 7 routes laser energy to an analysis sample 11 either through light compression device 9, such as a lens, or directly, depending on a selected operating mode. Collection optics 19 receives the response of the analysis sample through a fiber optic medium 17. Collection optics 19 provides signals to detection system 21, which drives monitor 23. Monitor 23 may be used alone or in conjunction with a data storage device (not shown) for further analysis and study of the sample 11.

Figure 2:
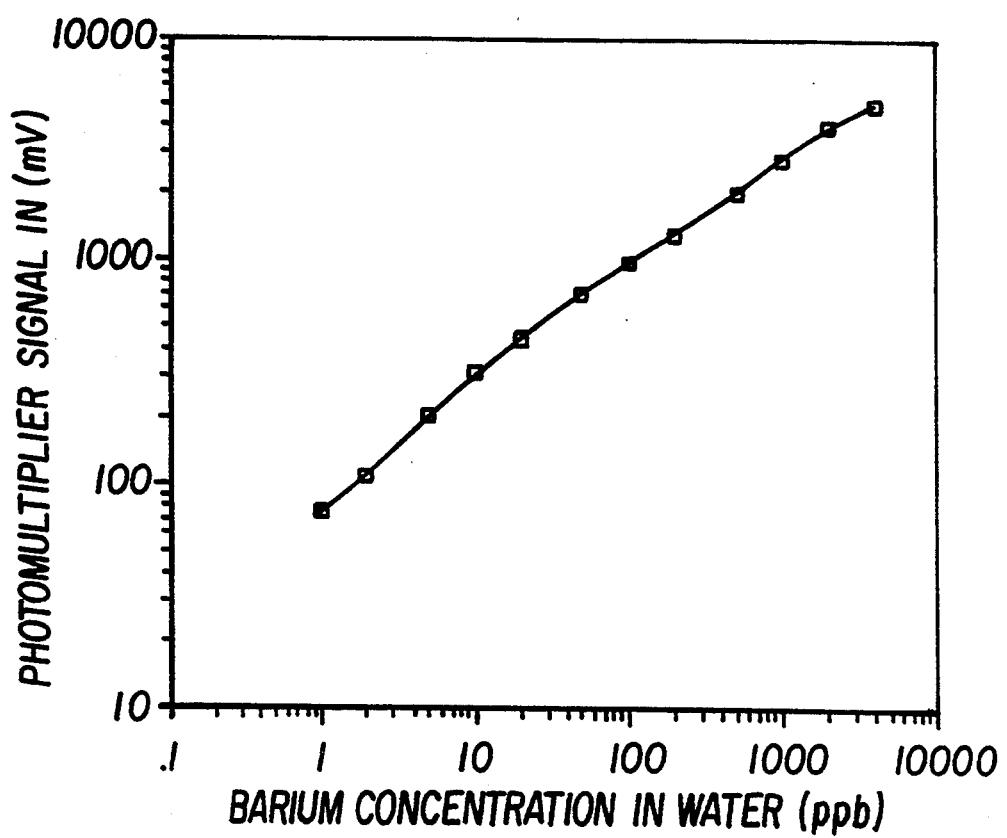
FIG. 2 shows results for detecting low concentrations of barium.

In the first operating mode, which is used for the detection of metals or other trace elements, distribution optics 7 routes laser energy to a light focusing device 9, such as a lens. The light is then directed to analysis sample 11, where a high temperature plasma is thus generated. In situ measurement using techniques similar to those of flame spectroscopy or ICP can then be employed. In flame spectroscopy, water is heated to temperatures in the order of several thousand degrees and the metals and other elements emit characteristic resonance lines, which are then used to detect low concentrations of such metals or other elements. For example, using the method of the invention, very low barium concentrations can be detected by collected characteristic lines, as illustrated by the relationship between photomultiplier signal strength and barium concentration shown in FIG. 2.

Figure 3:
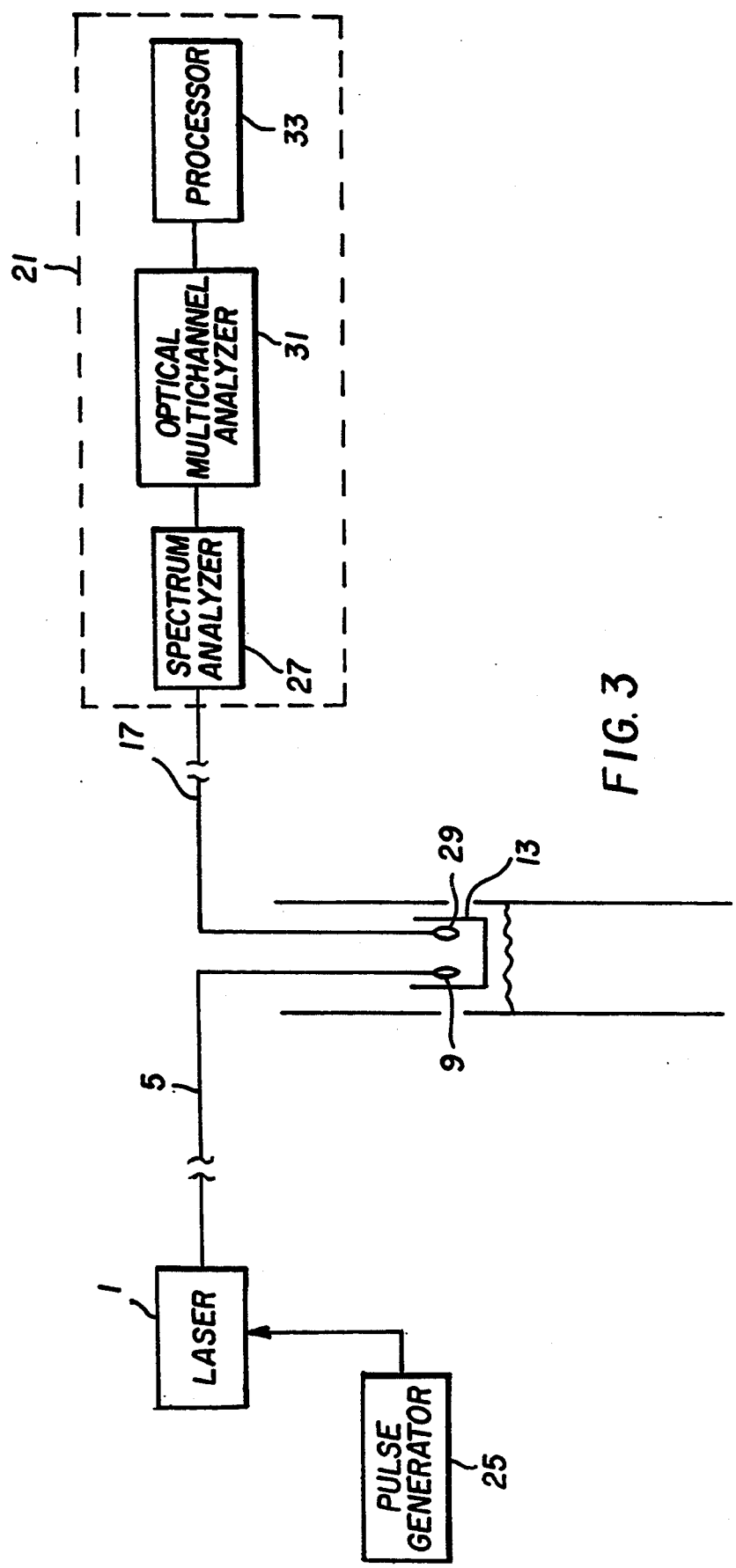
FIG. 3 is a simplified diagram of the invention in operation.

As shown in FIG. 3, according to the present invention a similar condition can be generated down in a well by using a laser spark. A penetrator 13, which contains light focusing device 9, is used. The penetrator 13 could be of the type that an analysis sample is taken into the penetrator for measurement. Alternatively, the penetrator 13 could be of the type that facilitates measurement of an analysis sample which remains in the well. For example, penetrator 13 could direct energy through an open bottom to the surface of the material to be analyzed in the well. In still another version of such a penetrator, the focusing lens 9 could be incorporated into the bottom of the penetrator. The specific penetrator used will depend on the application and conditions in the well and the sample.

The spark is generated by focusing the laser energy through light focusing device 9 in penetrator 13 onto a small spot on the surface of the water or soil serving as the analysis sample in the well or on the analysis sample within the penetrator 13, depending on the type of penetrator employed. Using an excimer laser emitting pulses of 0.01–0.10 microsecond duration at a pulse repetition rate of 100 pulses per second, at an average intensity on a water target of 10 kw/cm$^2$, the peak intensity during a single pulse is $10^8$–$10^9$ w/cm$^2$. For such a surface energy deposition rate, a layer of the analysis sample 11 will heat up rapidly to a very high temperature. For example, a temperature of over 5,000° K. would occur during one microsecond at an irradiation level of $10^7$ w/cm$^2$ in a layer having a thickness of $(2kt_e)^{\frac{1}{2}}$, where k is thermal diffusity and $t_e$ is the laser pulse length.

The radiant energy flux at the focal spot exceeds the breakdown threshold, and the heated gas in the absorbing layer expands and sends out a shockwave. Across the shockwave, the gas is heated and ionized. The absorption of light and energy release occurs behind of the shockwave. Under these conditions, the water and metal substances will be vaporized. The vapor may be partially ionized and the remaining neutral atoms will be in excited electron states. These conditions are similar to flame conditions. Thus, the presence of heavy metals or other trace elements can be detected by the appearance in the spectrum of the vapor of a very narrow characteristic line structure on the order of $\Delta\lambda/\lambda = 10^{-5}$. This wavelength structure can be used for element identification.

At still higher laser intensities, a plasma can be created with temperatures between 10,000° K. and 50,000° K. At this temperature range, the molecules are completely dissociated. This is useful, for example, to detect mercury or other metals in organic molecules, where it is very difficult to create sufficient current for evaporation with convention methods.

The laser induced spectrum from metallic substances or trace elements in analysis sample 11 is transmitted via fiber optic media 17 to collection optics 19. Collection optics 19 provides optical signals to detection system 21, which produces signals to drive monitor 23 and/or a memory device which can store the data for later analysis.

As FIG. 3 illustrates, the system is mobile because it uses an optical delivery system, e.g., fiber optic transmission media 5 and 17, to transmit the output of a pulsed laser, such as laser 1 pulsed by pulse generator 25, to penetrator 13 at a remotely located site, for example, down in a well. In order to detect metals and trace elements, moveable lens 9 is positioned to focus laser energy onto the sample and lens 29 is used to focus energy to be collected onto fiber optic media 17. Fiber optic media 17 then routes the collected optical information to spectrum analyzer 27.

As previously discussed, spectral lines identify substances in the analysis sample. Such a technique employs optical multichannel analyzer 31 and processor 33. Using this approach, a sample is heated to a plasma and allowed to cool down sufficiently long to radiate. A wide range of temperatures occurs during the relaxation process, which begins at the end of the laser pulse. Different temperatures are associated with molecule excitation, dissociation, atom and molecule ionization and recombination, electronic excitation and deexcitation. Excitation times, or the amount of time required for an ion to be excited to a state by an electron collision is significantly faster than the characteristic time for the existence of a particular ion.

For example, assume a hot plasma is ionized to the fourth stage of ionization during a laser pulse. In a preferred embodiment, a 7 nsec high intensity laser pulse generates extremely high temperature, for example up to $5 \times 10^{6}$° K. Once the laser pulse is removed, cool down starts. For example, during the next 100 nsec, the temperature drops to about 50,000° K. The temperature continues to decay and between about 4 $\mu$sec and about 10 $\mu$sec, the temperature drops to between about 10,000° K. and about 8,000° K. During this cool down atoms absorb electrons and move to lower stages of ionization. This process of catching electrons is called recombination. Signals emitted from the recombining plasma can be used to identify the substances in the sample.

Figure 4A:
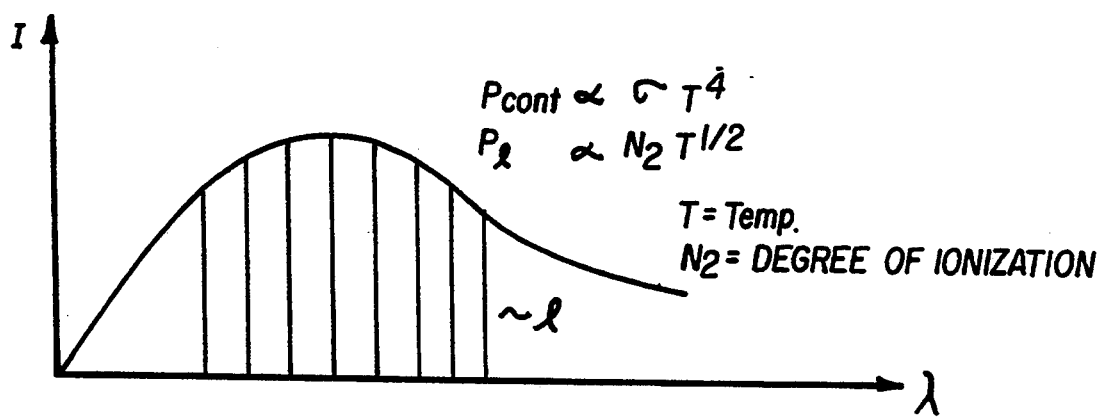
FIG. 4a shows continuous power and spectral line power relationships.
Figure 4B:
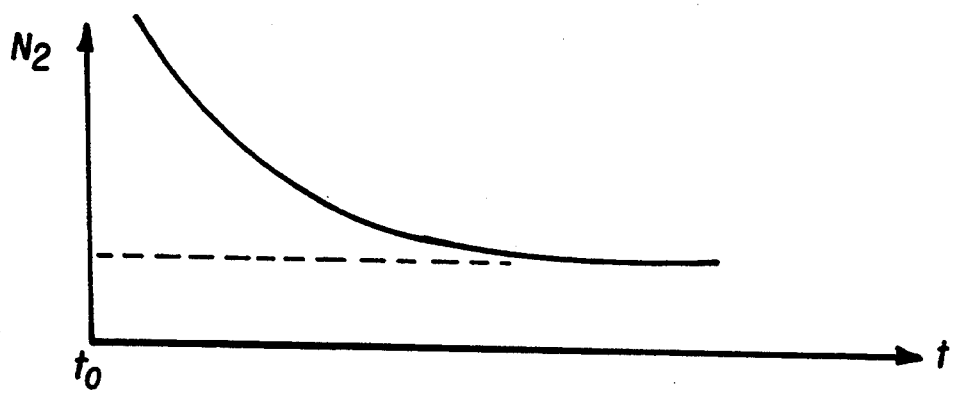
FIG. 4b illustrates the degree of excitation tending to a constant value.
Figure 4C:
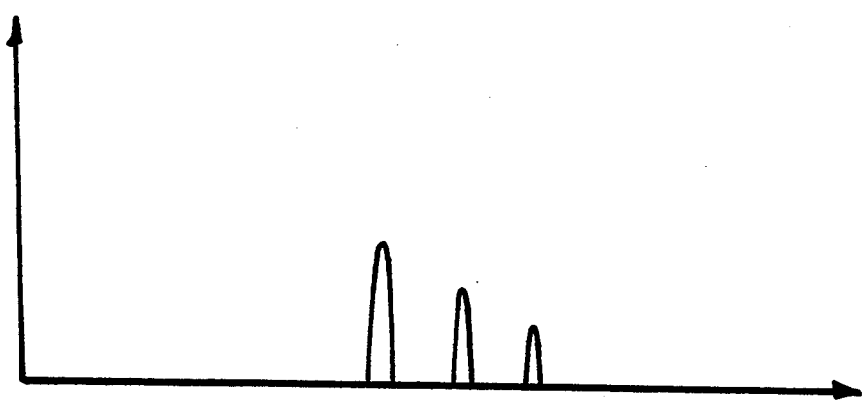
FIG. 4c shows the corresponding spectral lines used for detection.

FIGS. 4a–4c illustrate relationships that can be exploited to improve signal to noise ratio for detection of trace elements. Signal to noise ratio is proportional to the ratio between the power of a spectral line and continuous power. Thus, S/N is proportional to $P_t/P_{cont}$. FIG. 4a illustrates individual spectral lines and a continuous power curve and their relationships to temperature. As shown in FIG. 4b, as the plasma excited by the laser spark at $t_0$ cools down over time, rapid expansion retards recombination and the degree of ionization tends to a constant value. By this time, the plasma temperature responsible for the background is reduced. As shown in FIG. 4c, the spectral lines can still be detected. With the background reduced, the signal to noise ratio is improved during this time.

Processor 33 can be used to assist in the process of identifying the substances in the analysis sample. Characteristic spectral lines belonging to a singularly ionized or neutral element are analyzed and compared with known spectral characteristics stored in a data base. Such a data base can be generated for a particular system using control samples of substances to be identified or can be programmed to default characteristics. For example, a characteristic wavelength can be used to identify a particular substance. In cases where a characteristic wavelengths of different substances are very close, additional wavelengths can be examined to further evaluate the analysis sample for substance identification.

Concentrations of substances in the analysis sample can be determined based on line intensity. For example, optical multichannel analyzer equipment 31 can include an image intensified diode array or other circuitry which produces counts or other indications of element concentrations in the analysis sample. These counts or other indications can then be displayed and/or stored for further analysis. The count values or other indications can be compared to data stored in a data base of control samples or default data indicating concentrations of particular substances corresponding to the count values.

Figure 5A:
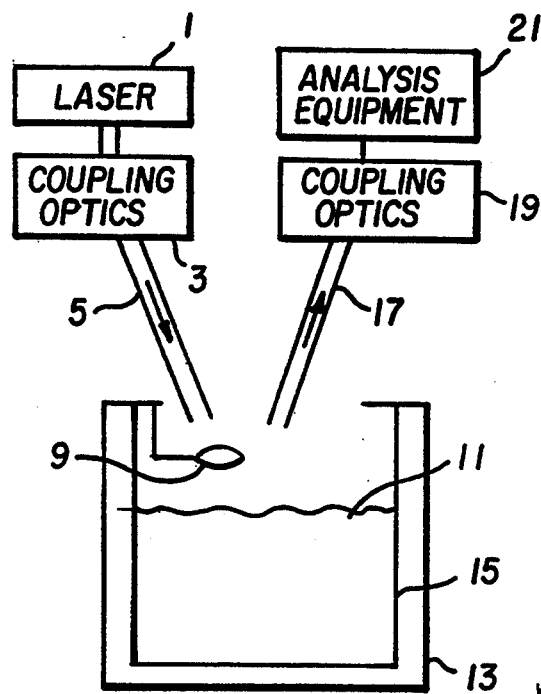
FIG. 5a illustrates a system with a focusing lens configured to operate in a first mode to generate a plasma for trace element detection.
Figure 5C:
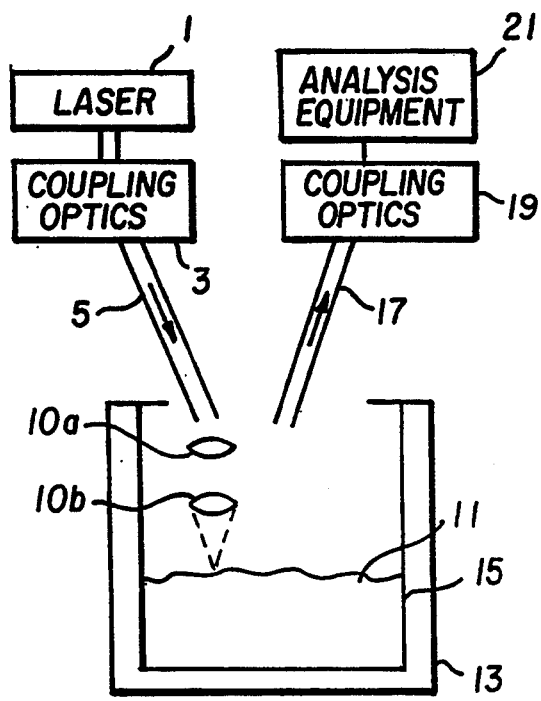
FIG. 5c illustrates a system configured with a plurality with focusing elements.
Figure 5B:
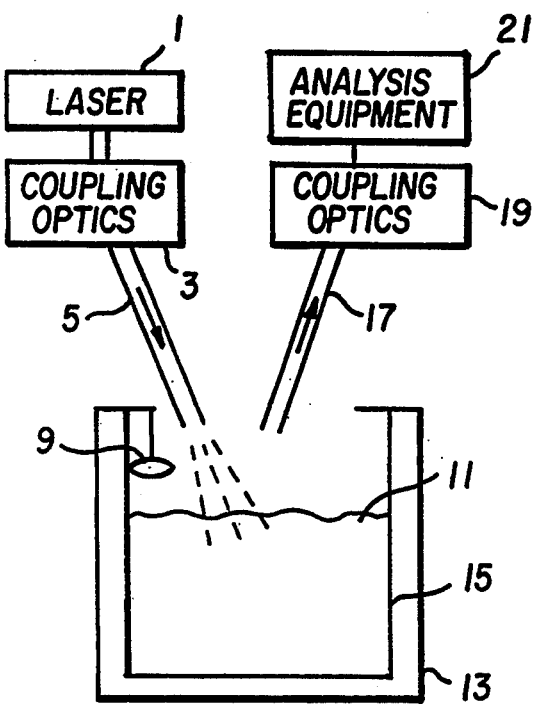
FIG. 5b illustrates a system with the focusing element removed from the input path for operation in a second or fluorescence detecting mode.

A system according to the invention can be operated in a second mode to detect fluorescence of the aromatic (ring) molecular structures of organic contaminants in an analysis sample of, for example, ground water or soil. In this mode, the focusing mechanism 9 is removed from the path of the light exiting from the fiber optic transmission media, so that an unfocused beam as shown in FIG. 5b is produced. The ring structure associated with aromatic molecular substances efficiently absorbs light and later emits the absorbed ultraviolet energy as fluorescence. Since the wavelength and temporal structure of the fluorescence are functions of the molecular structure, the type of material or pollutant can be identified. The intensity of the fluorescence is a function of the concentration of the substance or pollutant. Thus, in this second mode, distribution optics 7 provides laser energy to organic substances having aromatic molecular structures which fluoresce in analysis sample 11. Processor 31 can be employed using a data base of control samples or default values to identify the type and concentrations of substances in the analysis sample, as previously discussed.

Figure 6:
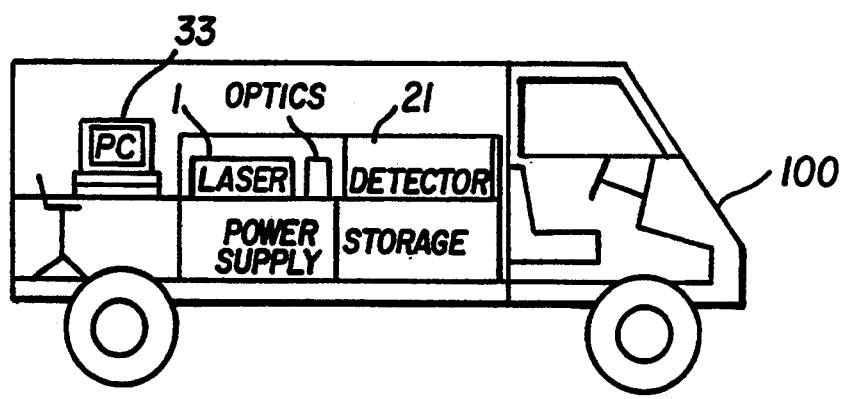
FIG. 6 illustrates a mobile laboratory according to the invention.

A system according to the invention can be configured to operate in both trace element detection and organic contaminant detection modes with a penetrator 13 for in the well or in the ground measurements, or to operate as a mobile lab 100 (FIG. 6). FIGS. 5a–5c illustrate several configurations of a system according to the invention. In FIGS. 5a and 5b, energy from laser 1 is coupled through coupling optics 3 and transmitted through fiber optic medium 5 toward an analysis sample 11 in penetrator 13. In FIG. 5a, lens 9, situated on a moveable arm 12 in penetrator 13, is positioned in the path of the light energy being carried from fiber optic medium 5, so as to focus energy on a specific spot of the analysis sample. This provides the high levels of heating necessary for the first operational mode discussed above.

FIG. 5b shows the lens 9 in a retracted position, thereby causing an unfocused beam to be directed at the sample in order to facilitate the second operational mode discussed above. In both FIGS. 5a and 5b, energy emitted from the sample 11 either as a laser induced spectrum from metallic substances or trace elements (the first operational mode) or by fluorescence (the second operational mode), is transmitted through fiber optic medium 17 and coupling optics 19 to analysis equipment 21.

FIG. 5c illustrates still another possible configuration according to the invention. In this case an analysis sample is analyzed in a fixed or mobile laboratory, using a pair of lenses 10a and 10b. Such a pair of lenses can also be employed in system configurations using penetrator 13. For example, both lenses can be placed on moveable arms. Alternatively, lens 10a, which acts to diffuse the energy over a larger sample can be stationary, while lens 10b, which acts to concentrate the energy on a small spot of the sample can be located on a moveable arm to be positioned in the light path as necessary.

It should be noted that it is not absolutely necessary to employ a penetrator. For example, a sample could be removed from a well and taken to the mobile lab set-up shown in FIG. 6 for further analysis.

In the mobile lab environment, analysis samples taken from the ground or water would be taken to the on site lab, as shown in FIG. 5c, for analysis. In this case the penetrator 13 would not be required as part of the analysis system. Samples brought to the mobile lab would be analyzed using the techniques described above, with an optical delivery system providing a focused laser beam generating a plasma in the trace element detection mode and a relatively unfocused beam being used to monitor fluorescence for detection of organic contaminants.

For use in a well, the fiber can be integrated into a penetrator 13 that allows delivery of the laser light into ground water or soil. Alternatively, the water can be collected into a cell 15, which is part of the penetrator and which is coupled to fiber optics transmission media 17, for transmission to collection optics 19. As shown in FIG. 5a, in this configuration the focusing lens is positionable to one of two positions. In the first mode, the lens is switched into a position which causes light carried from the pulsed laser and emitted from the fiber optic transmission media to be focused on a small portion of the surface of the sample. Since the second mode calls for a relatively unfocused beam (as compared with the first mode), the focusing device is switched to a second position, where it does not act to focus the light from the laser energy emitter on a relatively small point on the surface of the sample.

It is also possible to employ different penetrators or penetrator adapters for each operational mode. One type of penetrator or penetrator adapter would have a focusing mechanism which causes plasma generation, while another type of penetrator or penetrator adapter would be used for the second mode to create the relatively unfocused beam used to provide laser induced fluorescence. In addition, several other types of penetrators or penetrator adapters could be formed to achieve different levels of focusing and diffusion, as required. In some applications, the penetrator may be eliminated.

While specific embodiments of the invention have been described and illustrated, it will be clear that variations in the details of the embodiments specifically illustrated and described may be made without departing from the true spirit and scope of the invention as defined in the appended claims.

What is claimed is:

1. An apparatus for measuring the contents of an analysis sample comprising:
   a laser energy emitter;
   means for focusing energy emitted from said laser energy emitter on said sample, thereby generating excited electron states in a portion of said sample;
   means for measuring spectral characteristics of energy emitted from said sample when exposed to focused energy, measured ones of said spectral characteristics identifying substances in said analysis sample;
   means for defocusing said energy emitted from said laser energy emitter to induce fluorescence in said sample and thereby generate fluorescent energy; and
   a fluorescent energy detector for detecting the fluorescent energy.

2. The apparatus recited in claim 1, wherein said laser energy emitter comprises means for generating a laser spark.

3. The apparatus recited in claim 1, wherein said laser energy emitter comprises a pulsed laser, said pulsed laser emitting laser energy at a predetermined number of pulses per second, each pulse having a predetermined duration.

4. The apparatus recited in claim 3, wherein said laser energy has means for emitting single laser pulses having peak intensity between about $10^7$ W/cm$^2$ and $10^9$ W/cm$^2$.

5. The apparatus recited in claim 1, wherein said means for focusing comprises a lens.

6. The apparatus recited in claim 1, comprising means for storing spectral characteristics of predetermined substances and means for comparing measured spectral characteristics to stored spectral characteristics to identify substances in said analysis sample.

7. The apparatus recited in claim 1, comprising transmission media for carrying said laser energy to said analysis sample and energy emitted from said sample to said means for measuring said spectral characteristics.

8. The apparatus recited in claim 7, wherein said transmission media comprises fiber optic media.

9. The apparatus recited in claim 1, wherein trace elements are detected in said analysis sample by the presence of narrow spectral line characteristics.

10. The apparatus recited in claim 9, wherein the concentration of said trace elements in said analysis sample is determined by spectral line intensity.

11. An apparatus for measuring the contents of an analysis sample comprising:
    a laser energy emitter;
    means for focusing energy emitted from said laser energy emitter on said sample, thereby generating excited electron states in a portion of said sample;
    means for measuring spectral characteristics of energy emitted from said sample, measured ones of said spectral characteristics identifying substances in said analysis sample; and
    a fluorescent energy detector;
    wherein trace elements are detected in said analysis sample by the presence of narrow spectral line characteristics; and
    wherein the concentration of said trace elements in said analysis sample is determined by spectral line intensity.

12. The apparatus recited in claim 11, further comprising means for analyzing wavelength and temporal properties of said fluorescent energy, said wavelength and temporal properties characterizing organic substances contained in said analysis sample.

13. The apparatus recited in claim 12, wherein said emitter is located at a base remote from said analysis sample and further comprising a penetrator connected to a remote end of a transmission media, said penetrator comprising a cell coupled to said transmission media for collecting said analysis sample and wherein a remote end of said transmission media is positioned to receive energy from said analysis sample in said cell.

14. The apparatus recited in claim 13, wherein said transmission media comprises a first fiber optic medium delivering laser energy from said laser energy emitter to said sample and a second fiber optic medium delivering energy generated in said sample to said means for measuring spectral characteristics.

15. The apparatus recited in claim 1, wherein said emitter is located at a base remote from said analysis sample and further comprising a penetrator connected to a remote end of a transmission media, said penetrator comprising a cell coupled to said transmission media for collecting said analysis sample and wherein a remote end of said transmission media is positioned to receive energy from said analysis sample in said cell.

16. The apparatus recited in claim 15, wherein said transmission media comprises a first fiber optic medium delivering laser energy from said laser energy emitter to said sample and a second fiber optic medium delivering energy generated in said sample to said means for measuring spectral characteristics.

17. The apparatus recited in claim 1, further comprising means for analyzing wavelength and temporal properties of said fluorescent energy, said wavelength and temporal properties characterizing organic substances contained in said analysis sample.

18. The apparatus recited in claim 17, comprising means for detecting intensity of said fluorescent energy to determine concentration of organic substances in said analysis sample.

19. The apparatus recited in claim 18, comprising a memory for storing fluorescence properties of known organic substances and means for comparing detected characteristics of said fluorescent energy with corresponding properties stored in said memory to identify organic substances in said analysis sample.

20. A method of in situ measuring the content of an analysis sample, the method comprising the steps of:
    emitting laser pulses from a laser energy emitter;
    focusing energy emitted from said laser energy emitter on said analysis sample, thereby generating excited electron states at a portion of said sample;
    measuring spectral characteristics of energy emitted from said sample, measured ones of said spectral characteristics identifying substances in said analysis sample;

detecting metals in said analysis sample by the presence of narrow spectral line characteristics; and detecting organic substances in said analysis sample by the presence of fluorescent energy characteristics.

21. The method recited in claim 20, wherein analysis of signals representing said spectral line characteristics and said fluorescent energy characteristics is performed in a processor to identify substances in said analysis sample.

22. An apparatus for measuring the contents of an analysis sample comprising:

a laser energy emitter;

means for selectively focusing energy emitted from said laser energy emitter on said sample, thereby providing focused energy to said sample to generate a plasma at a portion of said sample in a first mode and providing unfocused energy to induce fluorescence in said sample in a second mode; and means for measuring spectral characteristics of emissions from said analysis sample, measured ones of said spectral characteristics identifying substances in said analysis sample.

23. The apparatus recited in claim 22 wherein said means for focusing energy comprises a lens positionable in a first position corresponding to said first mode and a second position corresponding to said second mode, wherein said lens concentrates the energy emitted by said laser energy emitter on a small spot area of said sample in said first position.

24. The apparatus recited in claim 23 wherein said means for focusing energy further comprises a fixed lens that diffuses the energy emitted by said laser energy emitter over an area of said sample that is larger than said small spot area when said positionable lens is positioned in said second position.

25. The apparatus recited in claim 22 wherein said means for focusing energy comprises first and second movable lenses, each positionable in a first position corresponding to said first mode and a second position corresponding to said second mode, wherein said first lens concentrates the energy emitted by said laser energy emitter on a small spot area of said sample when said first and second lens are positioned in their respective first positions, and said second lens diffuses the energy emitted by said laser energy emitter over an area of said sample that is larger than said small spot area when said first and second lens are positioned in their respective second positions.

26. A method of in situ measuring the content of an analysis sample, the method comprising the steps of:

selectively focusing energy emitted from a laser energy emitter on said analysis sample, thereby providing focused energy to form a plasma at a portion of said sample in a first mode and providing unfocused energy to induce fluorescence in said sample in a second mode; and measuring spectral characteristics of emissions from said analysis sample, measured ones of said spectral characteristics identifying substances in said analysis sample.

27. The method recited in claim 26 wherein the step of selectively focusing energy comprises positioning a lens in a first position corresponding to said first mode and a second position corresponding to said second mode, wherein said lens concentrates the energy emitted by said laser energy emitter on a small spot area of said sample in said first position.

28. The method recited in claim 26 further comprising the step of comparing a measured one of said spectral characteristic to entries in a data base having predetermined spectral characteristics of known substances stored therein and identifying a substance in said analysis sample as a result of said comparison.

* * * * *